(12) United States Patent
Xing et al.

(10) Patent No.: US 7,632,674 B2
(45) Date of Patent: Dec. 15, 2009

(54) APPARATUS FOR STIMULATING AN ANIMAL CELL AND RECORDING ITS PHYSIOLOGICAL SIGNAL AND PRODUCTION AND USE METHODS THEREOF

(75) Inventors: Wanli Xing, Beijing (CN); Zhe Yu, Beijing (CN); Guangxin Xiang, Beijing (CN); Liangbin Pan, Beijing (CN); Jing Cheng, Beijing (CN)

(73) Assignees: CapitalBiochip Corporation, Beijing (CN); Tsinghua University, Beijing (CN)

( * ) Notice: Subject to any disclaimer, the term of this patent is extended or adjusted under 35 U.S.C. 154(b) by 911 days.

(21) Appl. No.: 10/499,098

(22) PCT Filed: Nov. 29, 2002

(86) PCT No.: PCT/CN02/00856

§ 371 (c)(1),
(2), (4) Date: Dec. 30, 2004

(87) PCT Pub. No.: WO03/056321

PCT Pub. Date: Jul. 10, 2003

(65) Prior Publication Data

US 2005/0106708 A1  May 19, 2005

(30) Foreign Application Priority Data

Dec. 17, 2001 (CN) .............................. 01 1 40338

(51) Int. Cl.
*C12M 3/00* (2006.01)

(52) U.S. Cl. .............. 435/287.3; 435/4; 435/287.1; 435/385; 205/777.5

(58) Field of Classification Search ................. 435/385, 435/285.2; 607/50, 117, 118
See application file for complete search history.

(56) References Cited

U.S. PATENT DOCUMENTS

| 5,403,680 | A | | 4/1995 | Otagawa et al. |
| 5,810,725 | A | * | 9/1998 | Sugihara et al. ............. 600/372 |
| 6,032,062 | A | | 2/2000 | Nisch et al. |
| 6,095,148 | A | | 8/2000 | Shastri et al. ................ 128/898 |
| 6,762,050 | B2 | * | 7/2004 | Fukushima et al. ....... 435/287.9 |

FOREIGN PATENT DOCUMENTS

CN  1 057 400  1/1992

(Continued)

OTHER PUBLICATIONS

Aebischer et al., Brain Research (1987) 436(1):165-168.

(Continued)

*Primary Examiner*—William H Beisner
*Assistant Examiner*—Michael Hobbs
(74) *Attorney, Agent, or Firm*—Morrison & Foerster LLP

(57) ABSTRACT

The present invention provides an apparatus for stimulating an animal cell and recording its physiological signal and methods of making and using thereof. The purpose of the present invention is to provide an apparatus for stimulating an animal cell and recording its physiological signal that is efficient, convenient, and accurate. The apparatus for stimulating an animal cell and recording its physiological signal of the present invention comprises a poor conductive substrate, wherein on at least one surface of the substrate is provided at least one unit conductive polymer layer and at least one good conductive microelectrode.

13 Claims, 3 Drawing Sheets

FOREIGN PATENT DOCUMENTS

| | | |
|---|---|---|
| CN | 1 131 744 | 9/1996 |
| CN | 1 183 121 | 5/1998 |
| CN | 1 284 166 | 2/2001 |
| DE | 42 41 206 | 6/1994 |
| JP | 2002335945 | 11/2002 |

OTHER PUBLICATIONS

Ensell et al., Medical and Biological Engineering and Computing (2000) 38:175-179.
Fernandez et al., Brain Research (2000) 887:222-229.
Jimbo et al., Biological Cybernetics (2000) 83:1-20.
Jimbo et al., IEEE Transaction on Biomedical Engineering (1993) 40(8):804-810.
Kotwal and Schmidt, Biomaterials (2001) 22:1055-1064.
Maher et al., Journal of Neuroscience Methods (1999) 87:45-56.
Pine et al., A Cultured Neuron Probe, Proceedings of IEEE-EMBS Annual Meeting, Amsterdam, The Netherlands (1996) Nov. Paper # 421.
Rousche et al., Journal of Neuroscience Methods (1999) 90:57-66.
Schmidt et al., Proc. Natl. Acad. Sci. USA (1997) 94:8948-8953.
Tateno and Jimbo, Biological Cybernetics (1999) 80:45-55.
Warren et al., Neuroscience (2001) 105(1):19-31.
Office Action dated Apr. 20, 2006 from EP Application No. 02 785 015.5-2404, 3 pages.
Cui et al., Journal of Biomedical Materials Research (2001) 56(2):261-272.
Supplementary European Search Report for EP 02785015.5, mailed on Oct. 17, 2005, 5 pages.
Notice of Reasons for Rejection for Japanese Patent Application No. 2003-556795, mailed on Feb. 1, 2008, 4 pages.

* cited by examiner

APPARATUS FOR STIMULATING AN ANIMAL CELL AND RECORDING ITS PHYSIOLOGICAL SIGNAL AND PRODUCTION AND USE METHODS THEREOF

FIELD OF INVENTION

The present invention relates to an apparatus for stimulating, particularly electrically stimulating, an animal cell and recording its physiological signals, as well as methods of making and using such apparatus.

BACKGROUND OF THE INVENTION

The ability of controlling neuronal growth and differentiation will be useful for the study of the underlying mechanisms of the nervous system, the treatment of neuronal diseases, and the effective repair of damages to nerve tissues. It has therefore been the focus of scientific research for a long time.

After years of study, it was realized that electrical stimulation can enhance neurite outgrowth in vitro and enhance nerve cell regeneration in vivo. Work by other researchers has indicated that neurite outgrowth was enhanced on the surface of piezoelectric material (Aebischer, et al., Piezoelectric guidance channels enhance regeneration in the mouse sciatic nerve after axotomy, Brain Research, 1987, 436(1), 165-168). This effect has been attributed to the presence of surface-bound charges resulting from minute mechanical stresses on the material. The exact mechanism of the observation is not yet clear. One theory is that certain proteins or other molecules that are critical to neurite extension become redistributed in the electrical field. Alternatively, these proteins could have undergone conformational changes that are favorable to neurite extension.

Conductive polymers represent a new class of materials whose electrical and optical properties can be controllably varied over a wide range, often in a reversible manner. Conductive polymers are stable, can be used in physiological cell culture media or body fluid for extended time, and have good compatibility with neurons. (C. E. Schmidt, V. R. Shastri, J. P. Vacanti, R. Langer, Stimulation of neurite outgrowth using an electrically conducting polymer, Proc. Natl. Acad. Sci. USA, 1997, 94, 8948-8953). It was also shown recently that electrical stimulation of neurons using conductive polymers as conductive media enhances neurite outgrowth. (A. Kotwal, C. E. Schmidt, Electrical stimulation alters protein adsorption and nerve cell interactions with electrically conducting biomaterials, Biomaterials, 2001, 22, 1055-1064; C. E. Schmidt, V. R. Shastri, J. P. Vacanti, R. Langer, Stimulation of neurite outgrowth using an electrically conducting polymer, Proc. Natl. Acad. Sci. USA, 1997, 94, 8948-8953). Researchers have also implanted conductive polymers as a scaffold in vivo, and used electrical stimulus to connect severed nerve tissues under the guidance of the scaffold (V. R. Shastri, C. E. Schmidt, R. S. Langer, J. P. Vacanti, U.S. Pat. No. 6,095,148, Aug. 1, 2000). Use of microelectrodes or arrays of microelectrodes to record electrophysiological signals of neurons and nerve networks has been studied since the 1970's, and tremendous progress has been made in recent years. One way is to insert multiple microelectrodes into a live subject to measure extracellular signals. The electrodes can be in the shape of spikes, with multiple electrodes being a cluster of spikes (E. Fernandez, J. M. Ferrandez, J. Ammermuller, R. A. Normann, Population coding in spike trains of simultaneously recorded retinal ganglion cells, Brain Research, 2000, 887, 222-229; D. J. Warren, E. Fernandez, R. A. Normann, High resolution two-dimensional spatial mapping of cat striate cortex using a 100-microelectrode array, Neuroscience, 2001, 105(1), 19-31; P. J. Rousche, R. S. Petersen, S. Battiston, S. Giannotta, M. E. Diamond, Examination of the spatial and temporal distribution of sensory cortical activity using a 100-electrode array, Journal of Neuroscience Methods, 1999, 90, 57-66), or can be positioned in a cone, with each electrode being a planar electrode on the bottom surface of the cone (G. Ensell, D. J. Banks, P. R. Richards, W. Balachandran, D. J. Ewins, Silicon-based microelectrodes for neurophysiology, micromachined form silicon-on-insulator wafers, Medical & Biological Engineering & Computing, 2000, 38, 175-179); another method is to use a two-dimensional array of microelectrodes to simultaneously measure multiple measured cells cultured in vitro (Y. Jimbo, A. Kawana, P. Parodi, V. Torre, The dynamics of a neuronal culture of dissociated cortical neurons of neonatal rats, Biological Cybernetics, 2000, 83, 1-20; T. Tateno, Y. Jimbo, Activity-dependent enhancement in the reliability of correlated spike timings in cultured cortical neurons, Biological Cybernetics, 1999, 80, 45-55; M. P. Maher, J. Pine, J. Wright, Y. C. Tai, The neurochip: a new multielectrode device for stimulating and recording from cultured neuron, Journal of Neuroscience Methods, 1999, 87, 45-56); the third method is to make spikes containing the microelectrode arrays of the second method along with embryonic neurons, insert the spikes into a live subject, and observe the integration and communication of signals between cells on the microelectrode array and cells in the subject. (J. Pine, M. Maher, S. Potter, Y. C. Tai, S, Tatic-Lucic, J. Wright, A cultured neuron probe, Proceedings of IEEE-EMBS Annual Meeting, Amersterdam, the Netherlands, 1996, November, paper #421). The advantage of measuring signals in vitro is that one can control the positioning of the cell and the condition of the cell culture, thereby studying various functions of the neurons clearly and conveniently. However, the direction of neurite outgrowth is usually random and hard to control, which makes it difficult to establish a nerve network for the purpose of recording the communication of electrophysiological signals. It also makes it difficult for implanted neurons to integrate into the nervous system of the subject and communicate with the nervous system. Some researchers have mechanically forced neurons to grow only in defined channels. This kind of mechanical restriction, however, affects the normal outgrowth of neurites. Other researchers have used patterns formed by materials such as metal oxide to study the guidance of these materials on neurites (Yashihiko Jimbo, P. C. Robinson, Akio Kawana, Simultaneous Measurement of Intracellular Calcium and Electrical Activity from Patterned Neural Networks in Culture, IEEE transaction on biomedical engineering, 1993, 40(8), 804-810).

DETAILED DESCRIPTION OF THE INVENTION

The purpose of the present invention is to provide an efficient, convenient, and accurate apparatus for stimulating an animal cell and recording its physiological signal. To achieve such purpose, the present invention provides an apparatus for stimulating an animal cell and recording its physiological signal, such apparatus comprising a substrate comprising a poor conductive material, wherein on at least one face of the substrate is provided at least one unit conductive polymer layer and at least one good conductive microelectrode.

To prevent the conductive polymer from detaching from the substrate as result of extended exposure to culture media or body fluid, an intermediate layer between the substrate and the conductive polymer layer can be provided. Such intermediate layer can be made of gold or platinum. One function of the intermediate layer is to serve as a carrier for electrical polymerization. Another function is to allow conductive polymer to adhere strongly.

The substrate can be a two-dimensional planar structure; or it can contain one or more wells for positioning cells.

The material used to make the substrate can be rigid or flexible, and can be chosen from silicon, glass, polymer, or metal oxides.

The conductive polymer serves to guide the outgrowth of the neurites. Accordingly, the conductive polymers can form a grid-like pattern with disconnected junctions, with nerve cells at the junctions. The neurites will therefore grow along the conductive polymer pattern and communicate with each other. Because the diameters of neurites are usually 1-2 microns, the width of each band of conductive polymers is usually smaller than 5 microns. If the band is too narrow or too broad, the ability of the conductive polymers to guide the neurites properly will be affected. The pattern of the conductive polymers should be chosen in a way that facilitates the formation of nerve networks among the neurites.

The conductive polymer described herein can comprise multiple units. These units can be interconnected and share a single pair of stimulating electrodes. Alternatively, the units may not be connected with each other, each unit having their own pair of stimulating electrodes. If the units are not interconnected, the stimulating parameters (such as current intensity, duration, amplitude, and frequency) for each conductive polymer unit can be either the same or different.

The thickness of the conductive polymer layer described herein can be uniform or not uniform. The thickness of the conductive polymer layer can be between several nanometers to several millimeters. When the cells are to be observed in vitro under an inverse microscope, the thickness of the conductive polymer layer is preferably below 500 nanometers. This provides high light permeability and allows the polymers to properly adhere to the substrate.

The material that the conductive polymer can be made of includes polyaniline, polypyrrole, polythiophene or their derivatives, copolymers, or mixtures thereof. The conductivity of the conductive polymer can be adjusted according to spatial and temporal requirements. When microelectrodes are used to record electrophysiological signals, the conductive polymer layer can either be adjusted to be nonconductive or remain being conductive, as long as the measurement of the electrophysical signals is not affected.

The microelectrodes described herein may comprise more than one microelectrodes, which can be arranged into microelectrode arrays. The material from which the microelectrodes are made can be gold, platinum, or indium-tin oxide (ITO).

The conductive polymer layer and the microelectrodes described herein can be connected or not connected to each other. When not connected, the conductive polymer layer and microelectrodes can be about 1 to about 50 microns apart. The distance between conductive polymer and microelectrode in each unit can be the same or different.

To prevent the escape of cultured cells, the area above the substrate that is not covered by conductive polymers and is not the area for cell growth or microelectrode measurement can be coated with insulation materials. The insulation material can be made of nonconductive materials (such as polyimide or other materials with good biocompatibility) that are not toxic to cells. The thickness of the insulation layer is usually 5 to 100 microns.

Another purpose of the present invention is to provide a simple method of making the apparatus for stimulating animal cells and recording the physiological signals described above.

In one embodiment, the method of making an apparatus for stimulating animal cells and recording the physiological signals comprises the steps of: (a) depositing good conductive microelectrodes and their connecting wires on a substrate through evaporation or sputter; (b) depositing at least one unit of conductive polymer layer with a desired pattern on the substrate by PVD, CVD, electrical polymerization, or macromolecule self-assembly; and (c) depositing some metallic wires underneath the conductive polymer layer for connecting the conductive polymers to the stimulating electrodes.

Another purpose of the present invention is to provide a method of using an apparatus for stimulating animal cells and recording physiological signals.

In one embodiment, the method of using an apparatus for stimulating animal cells and recording physiological signals comprises the steps of: (a) passing electrical current through conductive polymers either continuously or intermittently, wherein the electrical stimulation can be direct current or alternating current, wherein the electric current intensity can be of pA to mA scale, and wherein for alternating current stimulation, the stimulation frequency can be $1-10^6$ Hz; and (b) recording physiological signals generated from cells being tested through the microelectrodes by measuring electrical current, electrical potential, or impedance electrical signals.

The apparatus for stimulating animal cells and recording physiological signals described herein can be two dimensional squares, circles, or any other irregular shapes. In other embodiments, the apparatus is a three-dimensional hollow cylinder, a globe, a cubic, a cuboid, a cone, or any other irregular shapes.

The present invention is further illustrated through the following description of the figures and example.

EXAMPLES

Example 1

Making of the Apparatus of the Prevent Invention

On one surface of a 350 micron-thick square glass substrate, use routine photoetching method to produce a 300-nm thick layer of gold, with measuring microelectrodes, stimulating electrodes, and connecting wires with a desired pattern.

Apply electricity to the stimulating electrodes. Use electrochemical polymerization methods to form a 100 nm-thick layer of polyaniline conductive polymer on top of the gold layer that is connected to the stimulating electrodes, forming the desired pattern.

Use spin-coating method to create an insulation layer on the top. Use photoetching method to generate the desired structure.

An apparatus for stimulating animal cells and recording its physiological signals can be made using the above method.

In this example, the substrate can be chosen from a wide range of materials, as long as it is a poor conductive material. The thickness and shape of the substrate can be chosen according to the needs of the experiment. To make efficient use of the space, more than one surface of the substrate can be utilized as described above. The electrode layer can be made of platinum, ITO, or other kinds of good electrically conductive materials. The thickness of the electrode layer is preferably between 30 nm to 400 nm. The material from which the conductive polymers are made of can be chosen from a wide variety of materials, and depends on the needs of the experiment. For example, the material can be polyaniline, polypyrrole, polythiophene, or their derivatives, copolymers, or mixtures thereof. Other methods of coating or photoetching can also be used to generate electrodes and conductive polymer layers and to form desired patterns.

Example 2

Structure of the Present Invention

Figure 1:
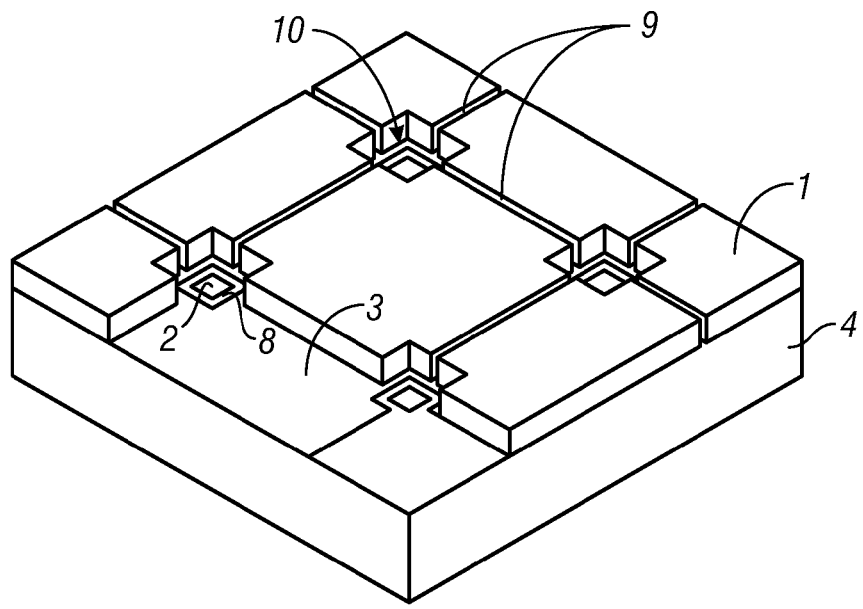
FIG. 1 provides a structural diagram of a subregion of an apparatus of the present invention.
Figure 2:
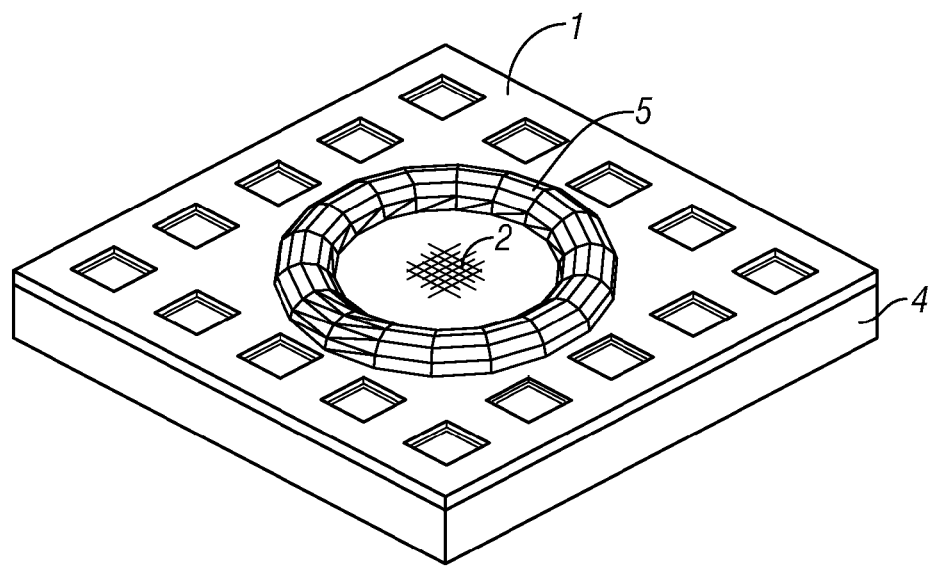
FIG. 2 provides an overview of an apparatus of the present invention.
Figure 3:
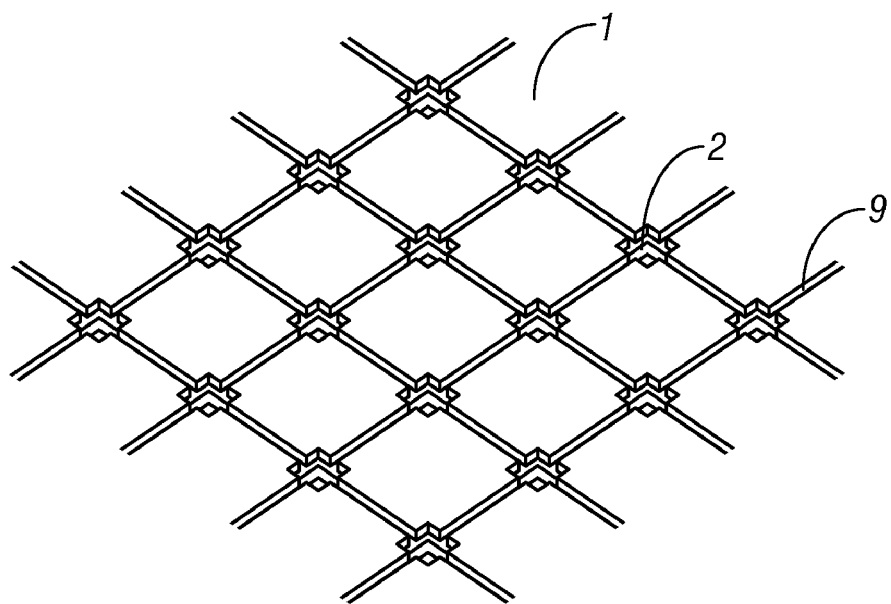
FIG. 3 provides a magnified view of microelectrode arrays.

As shown in FIGS. 1, 2, and 3, the apparatus for stimulating animal cells and recording its physiological signals comprises the 400 micron-thick square silicon substrate 4; the 100-micron thick polypyrrole conductive polymer layer 3 on top of substrate 4, the conductive polymer layer being connected to two electrodes (not indicated in this figure); the sixteen 40 nm-thick platinum microelectrodes 2 on top of substrate 4, each microelectrode having an output electrode (not indicated in this figure). There is a 25-micron gap (8) between the conductive polymer 3 and the microelectrode 2. Areas on substrate 4 that are not covered by conductive polymers 3 and are not areas for cell growth (10) or microelectrodes measurement are covered by a polyimide insulation layer 1. The insulation layer has a thickness of 10 microns, forming a 3-7 micron-wide channel (9) that prevents cells from escaping.

As shown in FIG. 2, there is a small cell culture chamber 5 on top of the substrate for holding cell culture media. The chamber is made of biocompatible materials such as polyimide. The height of the culture chamber 5 is usually bigger than 100 mm, and the area of the chamber depends on the number and distribution of the microelectrodes in the microelectrode array.

In this example, there is an intermediate layer between the substrate and the conductive polymer layer (not shown in the figure) for preventing the conductive polymer layer from detaching from the substrate as a result of extended exposure to the culture medium or body fluid.

Figure 5:
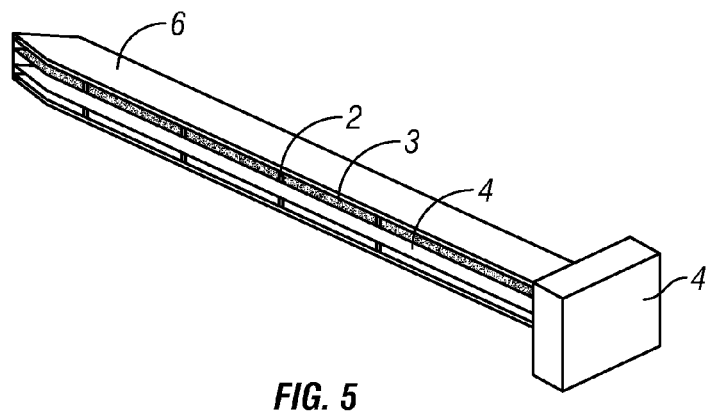
FIG. 5 provides a three dimensional diagram of an apparatus of the present invention that is used for implanting into a live subject.

In the present example, the size and shape of the apparatus, as well as the choice of the surface or surfaces of the substrate for depositing conductive polymer layers or microelectrodes, are determined by the needs of the experiment. As shown in FIG. 5, to facilitate the use of the apparatus in vivo, the two lateral sides of the substrate 4 are both covered with conductive polymer layer 3 and microelectrodes 2. Neurons can be placed on both sides of the substrate, thus to increase cell density and enhance efficiency. As shown in FIG. 5, the apparatus for implanting in vivo contains a top layer 6. This layer is useful for preventing cell damages during implanting and preventing cells from escaping in the live subject. The material from which layer 6 is made of is preferably biocompatible, stable, and nonconductive (such as polyimide).

Example 3

Use of the Apparatus of the Present Invention to Study Nerve Network in vitro

Figure 4:
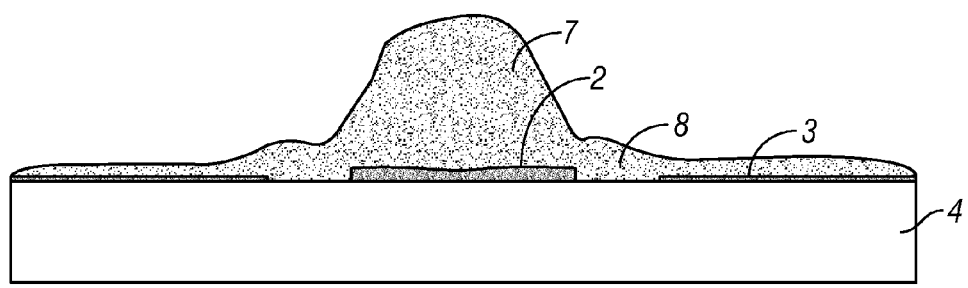
FIG. 4 provides a sectional view of a single culture unit used for studying nerve networks in vitro.

Place neuron 7 on the apparatus as shown in FIG. 4. Introduce electrical current intermittently through the conductive polymer. The electrical stimulation can be direct current or alternating current, and the stimulation frequency can be $1\text{-}10^6$ Hz. The physiological signals of the cell being studied are measured through microelectrode 2.

After the intermittent electrical stimulation (constant voltage at 100 mV), and culturing of the cells for several days, the growth of the stimulated cells, as measured by parameters such as the size of the cell body, the length of the neurites, is measured and compared with those of unstimulated cells. In addition, cells are stimulated by electrical or chemical signals, and the response of the cells to the various stimulations is monitored through the microelectrodes, by measuring the changes of the electrical potential on the cell membrane.

Example 4

Use of the Apparatus to Study Nerve Network in vivo

Implant the apparatus as shown in FIG. 5 into a live subject. The neuronal network on the apparatus is used to connect damaged nerve fibers in the subject. The apparatus is also used to measure the response of neurons in local nerve tissues to external stimuli (including electrical and medicinal stimuli). Furthermore, the apparatus can be used to electrically stimulate local nerve tissues, thereby stimulate the repair and regeneration of damaged nerves.

Industrial Utility

The present invention applies conductive polymer and microelectrode fabrication technologies to neural science, and utilizes electrical stimulation through conductive polymers to effectively control the speed and direction of neurite outgrowth. This allows effective recording of electrophysiological signals of nerve network in vitro, and makes it possible to further study signal transduction and underlying mechanisms of the nervous system. The present invention also provides an implantable apparatus that allows the implantation of nerve cells in vivo, integration of implanted nerve cells with the main nerve system, and repair of damaged nerve tissues. The apparatus therefore has important medical application values. It is also expected that the apparatus will be useful for the treatment of urine incontinence, retina injury, or other neuronal diseases.

The apparatus of the present invention is not only useful for the study of different kinds of cells derived from various animal nervous systems, but also useful for the study of cells derived from non-neuronal cells.

We claim:

1. An apparatus for stimulating an animal cell and recording its physiological signals, said apparatus comprising:
   a poorly conductive substrate;
   at least two microelectrodes on said substrate;
   a band of conductive polymer comprising an electrical conductor, where the band of conductive polymer is between two microelectrodes and either is connected with each microelectrode or is separated from each microelectrode by a gap of 1-50 microns;

wherein the area above the substrate that is not covered by a band of conductive polymer, and is not an area for cell growth or a microelectrode, is coated with an insulation material layer that forms a channel around the band of conductive polymer and microelectrodes.

2. An apparatus for stimulating an animal cell and recording its physiological signals according to claim 1, wherein the band of conductive polymer is on an intermediate layer of gold or platinum.

3. An apparatus for stimulating an animal cell and recording its physiological signals according to claims 1, or 2, wherein the conductive polymer bands form a grid-like pattern with disconnected junctions, having a microelectrode at each junction;

wherein the conducting polymer is separated from the microelectrode by a gap of 1 to 50 microns.

4. An apparatus for stimulating an animal cell and recording its physiological signals according to claims 1, or 2, wherein the conductive polymer layer comprises multiple units that are connected to each other and share a single pair of stimulating electrodes.

5. An apparatus for stimulating an animal cell and recording its physiological signals according to claims 1, or 2, wherein the conductive polymer layer comprises multiple units that are not connected to each other, each unit comprising a pair of stimulating electrodes.

6. An apparatus for stimulating an animal cell and recording its physiological signals according to claim 1, wherein the conductive polymer layer is made of polyaniline, polypyrrole, polythiophene or their derivatives, copolymers, or mixtures thereof.

7. An apparatus for stimulating an animal cell and recording its physiological signals according to claim 1, said apparatus comprising more than one microelectrodes, wherein said microelectrodes are arranged in a microelectrode array.

8. An apparatus for stimulating an animal cell and recording its physiological signals according to claim 1, wherein the material for making the microelectrode is gold, platinum, or indium-tin oxide (ITO).

9. An apparatus for stimulating an animal cell and recording its physiological signals according to claim 1, wherein the conductive polymer is connected with the microelectrode.

10. An apparatus for stimulating an animal cell and recording its physiological signals according to claim 1, wherein the conductive polymer is separated from the microelectrode by a gap of 1 to 50 microns.

11. A method of making an apparatus for stimulating an animal cell and recording its physiological signals, comprising: (a) depositing good conductive microelectrodes and their connecting wires on a poorly conductive substrate through evaporation or sputter;

(b) depositing a conductive polymer layer with a desired pattern on the substrate by PVD, CVD, electrical polymerization, or macromolecule self-assembly, wherein the conductive polymer is connected with the microelectrodes or is separated from the microelectrodes by a gap of 1-50 microns; and (c) depositing some metallic wires underneath the conductive polymer layer for connecting the conductive polymers to stimulating electrodes;

and applying to the area above the substrate that is not covered by a band of conductive polymer, and is not an area for cell growth or a microelectrode, an insulation material layer that forms a channel around a band of the conductive polymer and the microelectrodes.

12. A method according to claim 11, further comprising the step of depositing an insulation layer with desired pattern by photoetching, wherein said step occurs before the step of depositing the conductive polymer layer.

13. A method of using the apparatus of claim 1 for stimulating an animal cell and recording its physiological signals, comprising the steps of (a) placing nerve cells on the microelectrodes, and passing electrical current through said conductive polymers either continuously or intermittently for several days to promote neurite outgrowth along bands of the conductive polymer, wherein the electrical stimulation is direct current or alternating current, wherein the electric current intensity is of pA to mA scale, and wherein for alternating current stimulation, the stimulation frequency is $1\text{-}10^6$ Hz;

and (b) recording physiological signals generated from cells being tested through the microelectrodes by measuring the electrical current, electrical potential, or impedance electrical signals.

* * * * *

UNITED STATES PATENT AND TRADEMARK OFFICE
CERTIFICATE OF CORRECTION

PATENT NO. : 7,632,674 B2  Page 1 of 1
APPLICATION NO. : 10/499098
DATED : December 15, 2009
INVENTOR(S) : Xing et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1385 days.

Signed and Sealed this

Second Day of November, 2010

David J. Kappos
*Director of the United States Patent and Trademark Office*